United States Patent [19]

Kung

[11] Patent Number: 4,832,599
[45] Date of Patent: May 23, 1989

[54] PERIODONTAL PROBE

[75] Inventor: Robert T. V. Kung, Andover, Mass.

[73] Assignee: Abiomed, Inc., Danvers, Mass.

[21] Appl. No.: 25,164

[22] Filed: Mar. 12, 1987

[51] Int. Cl.$^4$ .............................................. A61C 3/00
[52] U.S. Cl. ..................................... 433/32; 128/736; 374/155; 374/185
[58] Field of Search ................... 128/736; 433/32, 27, 433/72, 75, 147, 127; 374/141, 155, 183, 185, 201

[56] References Cited

U.S. PATENT DOCUMENTS

| | | | |
|---|---|---|---|
| 3,552,210 | 1/1971 | Wright | 374/184 X |
| 3,738,479 | 6/1973 | Sato | 206/16.5 |
| 3,935,640 | 2/1976 | Cohan | 433/75 |
| 4,280,508 | 7/1981 | Barrada | 128/736 |
| 4,501,555 | 2/1985 | Ditchburn | 433/72 X |
| 4,537,573 | 8/1985 | Sunada | 433/32 |
| 4,580,909 | 4/1986 | McIntosh | 374/208 X |
| 4,614,443 | 9/1986 | Hamert | 374/208 X |

FOREIGN PATENT DOCUMENTS

| | | | |
|---|---|---|---|
| 2448714 | 10/1980 | France | 128/736 |
| 0018425 | 1/1984 | Japan | 128/736 |
| 0957851 | 9/1982 | U.S.S.R. | 128/736 |

OTHER PUBLICATIONS

Annual Session, American Association for Dental Research, Abstract No. 527 Journal of Dental Research, vol. 65, Special Issue, 1986.
*Does A Temperature Gradient Exist Across the Mucogingival Junction?* N. Brill, et al. Journal of Oral Rehab. 1978, vol. 5, pp. 81–87.
*The Temperature of the Gingival Sulci.* S. Mukherjee J. Periodontal. vol. 49, No. 11, Nov. 1978, pp. 580–584.

Primary Examiner—Albert J. Makay
Assistant Examiner—Carl D. Price
Attorney, Agent, or Firm—Lahive & Cockfield

[57] ABSTRACT

A periodontal probe has a probe finger extending from a handle to an L-shaped distal end which includes a probe stem portion adapted for insertion into a periodontal pocket and formed of a thermally insulative material. A temperature sensing element is mounted at the extreme end of the stem portion. Conductive leads extend from the sensing element, through the probe tip to the handle. In a preferred embodiment, the temperature sensor is a thermistor which, together with the probe stem portion, is sealed within an epoxy outer skin. The tip tapers so that the thermal mass of the probe in the vicinity of the sensing element quickly attains the temperature of surrounding tissue while minimally perturbing that temperature. The handle contains signal processing and temperature display units, and the probe tip includes graduations for indicating probe depth. Interchangeable sensor matching circuit elements adapt sensor elements having different characteristics to a common display driver.

10 Claims, 2 Drawing Sheets

PERIODONTAL PROBE

The present invention relates to clinical periodontal instruments, and to the diagnosis of periodontal disease.

It is known in medicine generally to diagnose certain conditions of internal infection or inflammation by sensing the distribution of temperature over regions of the body, and identifying regions of abnormally high temperature as affected.

Some researchers have made measurements of periodontal pocket temperatures, which appear to vary greatly. Because of this large variation, one might expect a temperature-plotting approach to be of limited diagnostic utility in periodontics.

Owing to the physiological structure of the jaw, there are fairly large temperature gradients, from posterior to anterior regions, and from buccal to lingual sites on each side of the jaw. The presence of surface cooling due to breath air flow may further complicate the determination of even a normal temperature distribution. The combined effect of these sources of temperature variation is to mask from observation temperature anomalies which are less than approximately one-half degree Celsius. This would appear to limit the clinician's ability to identify with precision sites having temperature anomalies.

SUMMARY OF THE INVENTION

The present invention overcomes the foregoing limitations of the prior art by providing a periodontal probe having a handle and a probe finger extending from the handle to an L-shaped distal end. The distal end includes a probe stem portion adapted for insertion into a periodontal pocket and formed of a thermally insulative material, and a temperature sensing element mounted at the extreme end of the stem portion. Conductive leads extend from the sensing element, through the probe tip to the handle. In a preferred embodiment, the temperature sensor is a thermistor which, together with the probe stem portion, is sealed within an epoxy outer skin. The tip tapers to approximately (0.016) inches diameter, so that the thermal mass of the probe in the vicinity of the sensing element quickly attains the temperature of surrounding tissue while minimally perturbing that temperature. A prototype attains 0.10 °C. accuracy with a 0.2 second response time.

In an illustrated prototype, the handle contains signal processing and temperature display units. Preferably, the probe tip includes graduations for indicating probe depth. Preferred signal processing circuitry includes sensor matching circuit elements, for adapting sensor elements having different characteristics to a common display driver.

BRIEF DESCRIPTION OF THE DRAWINGS

These and other features of the invention will be understood from the following description of an illustrative embodiment, with reference to the drawings.

DESCRIPTION

Figure 1:
FIG. 1 shows a perspective view of a probe according to the invention.

FIG. 1 shows a perspective view of a prototype periodontal probe 1 according to the invention, having a handle portion 2 and a probe finger portion 3 extending from the handle. Finger portion 3 extends from a base end 4, which is firmly mounted in the handle, to a distal probe end 5 which has a general size and contour for probing a periodontal pocket.

At the distal end 5 of probe finger 3 a stem portion 7 having a length of approximately 1 cm. extends to a tip having a temperature sensing element 9 mounted thereat. Stem portion 7 is oriented transverse to the direction of base end 4, which in turn extends along the longitudinal axis of the handle portion 2.

The overall size and shape of the probe 1 are substantially those of a Michigan "O" probe, and the base end 4 of the probe finger may be fabricated of metal. The handle 2, as discussed further below, houses signal conditioning and display circuitry for converting the temperature sensor output to a temperature display, and includes a power on switch 11 and three digit temperature display 13. Probe finger 3 attaches to handle 2 by a multi-contact electrical twist-connect fitting 15. Conductive leads (not shown) extend from the temperature sensing element, through the stem and finger to the fitting 15.

The probe stem is formed of a material having low thermal conductivity, such as a polyimide or epoxy compound, thus isolating the temperature sensor from the main body of the probe finger. Preferably, the probe stem material has a thermal conductivity less than $10^{-2}$ watts/cm. °C. Applicant has found that the thermal conductivity of prior art probe fingers significantly perturbs the local temperature and limits the achievable accuracy of measurement and the response time.

Figure 2A:
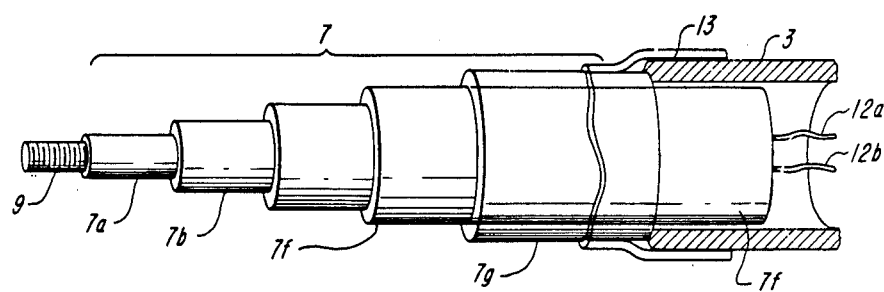
FIGS. 2A, 2B show details of the probe tip construction of one prototype probe similar to that of FIG. 1.

FIG. 2A shows a partial cutaway detail of construction of one probe tip having the desired strength and low thermal conductivity, employed in a prototype periodontal probe. As shown, finger portion 3 is formed from a 20 gauge thin-walled hypodermic needle, and stem portion 7 is made of a plurality of telescoping tubing segments 7a, 7b...7f, 7g formed of a commercially-available polyimide tube stock. The largest tube has a diameter of approximately (0.036) inches and forms a shoulder against the end of the metal needle 3, and one or more of the smaller tube segments 7f...extends into needle 3. The telescoping tube segments form a stem which tapers from approximately (0.036) inches down to approximately (0.014) inches at the sensor end. Sensor 9 fits into the central bore of the smallest tube segment 7a.

During assembly, the conductive leads 12a, 12b of the sensor assembly 9 are passed through each tube as the tube segment is placed over the preceding segment. The wires are then passed through the bore of the needle bore, and cement is placed about the protruding portion of tube 7f and shoulder of tube 7g to secure the stem assembly into the needle. A thin plastic tube segment 13, which may be, for example, (0.002) inch mylar is then heat-shrunk about the stem-finger joint to secure the components during further assembly.

Figure 2B:
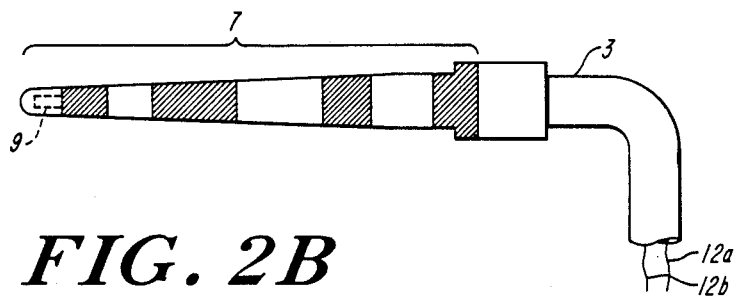

FIG. 2B shows the probe stem and tip assembly of FIG. 2A after fabrication. The telescoping tapered stem and sensor unit 7, 9 is potted to form an epoxy-sealed assembly. One suitable epoxy is the epoxy resin sold as Shell 828, with a Versamid 140 hardener. Following potting, Williams markings are painted on the sealed, tapered assembly to show depth of penetration of the sensor 9, which is indicated in phantom. As shown, the markings are graduated to one centimeter, although longer probes may be constructed.

Figure 3:
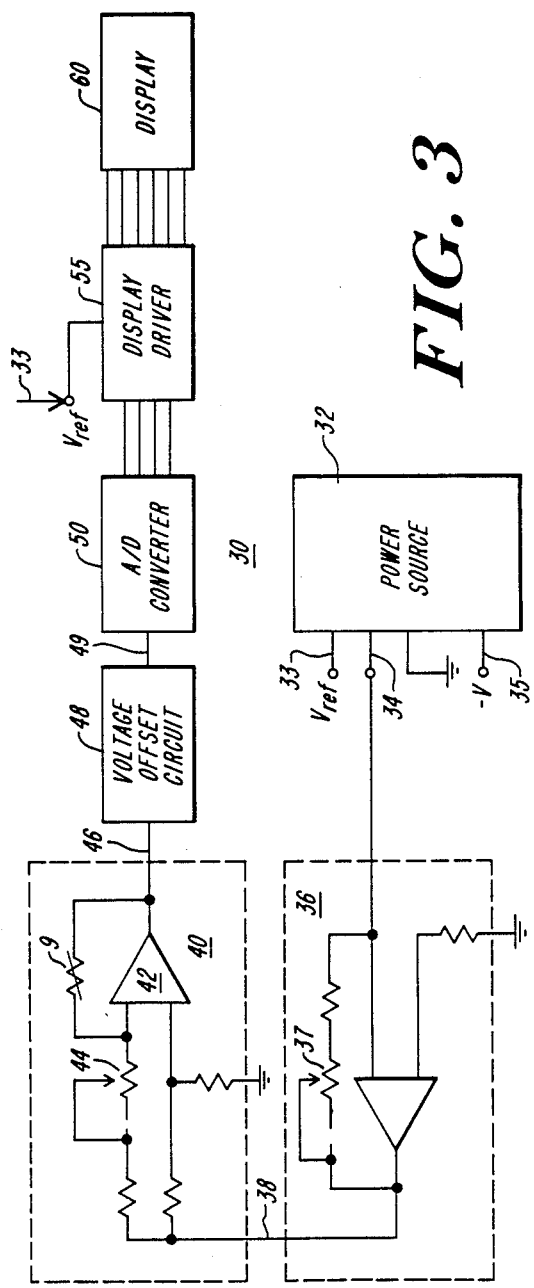
FIG. 3 is a schematic diagram of the temperature sensing and display circuitry.

FIG. 3 shows a block diagram of a circuit 30 used in a prototype embodiment of the probe. Circuit 30 includes a power supply 32, which provides a fixed reference voltage at output 33 and a drive and a( − ) voltage at outputs 34, 35 from a battery source. Voltage outputs 33, 34, 35 are achieved by providing a zener diode shunt to achieve a fixed voltage drop, which is then passed to a center-grounded voltage-dividing network in a manner known in the art. The drive voltage from output 34 passes to a voltage setting section 36 including an op amp with a feedback potentiometer 37 for adjusting amplifier gain so as to provide a selected stable output voltage along line 38.

The voltage on line 38 passes to a temperature sensing circuit 40 in which a second op amp 42 having a thermistor temperature sensor 9 in a feedback loop is adjusted, via second potentiometer 44 in a resistance bridge, so that the circuit 40 produces a zero volt output on line 46 when the thermistor 9 is at thirty seven degrees Celsius.

The potentiometers 37, 44 are adjusted upon assembly, with potentiometer 37 adusted in accordance with the gain characteristics of sensing circuit 40 — e.g., to provide a voltage which increases inversely to the nominal resistance of the selected thermistor 9 — and with potentiometer 44 set such that a zero volt signal appears on line 46 at the desired nominal 37 degree temperature. The voltage on line 46 then varies, in a substantially linear fashion, as the temperature of the thermistor changes.

Thermistor 9 has a resistance in the range of 30–60 kilohms, and draws a steady state current which is sufficiently low to not perturb the temperature readings by internal heat generation. The temperature indicative voltage signal on line 46 passes to a voltage offset circuit 48, which increments the voltage on line 46 by a fixed voltage offset to produce an offset temperature-indicating signal on line 49. The signal on line 49 is digitized and scaled with respect out the reference line 33 by analog to digital converter 50, and the scaled digitized signal passes to a display driver 55 which drives a display 60. In the embodiment shown in FIG. 1, the display displays temperature readings in one-tenth degree increments.

In a preferred embodiment, the probe finger and tip assembly 3 as shown in FIG. 1 is a removable interchangeable tip assembly which connects to the handle 2 by an electrical-contact type twist lock connector. In that embodiment, the potentiometers 37, 44, which in the prototype are used to match the nominal resistance and resistance gradient characteristics of the thermistor so as to produce an accurately scaled voltage to temperature reading, are replaced by one or more fixed resistance pairs 37a, 44a, 37b, 44b,..., each pair being matched to the characteristics of a single thermistor tip assembly.

Figure 4:
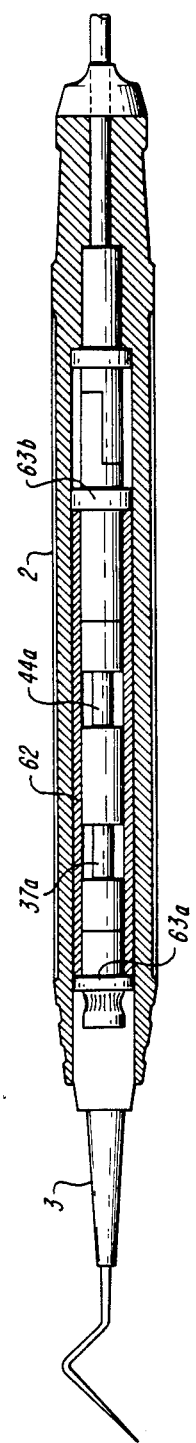
FIG. 4 is a section through a probe having interchangeable sensor units.

FIG. 4 shows a section through such a preferred embodiment. As shown, handle 2 contains a resistor cartridge 62 holding one or more pairs of matched resistors 37a, 44a,..... Cartridge 62 has a first end 63a adapted to engage the connector of probe tip 3, and a second end 63b which, upon engagement of the twist-locking probe tip connector places the correct pair of matched resistors into electrical contact with the voltage setting and temperature sensing circuitry. This allows replacement of tip assemblies, and permits the fitting of replacement temperature sensors, or temperature sensors adapted to detect finer temperature variations, or to accurately detect temperature variations centered about a different nominal center temperature.

It will be appreciated that the foregoing periodontal probe has been described with reference to the illustrated prototype embodiment and preferred variations thereof, but that the invention is not limited thereto. In other embodiments different temperature sensing elements, and corresponding signal conditioning circuitry may be employed, and different probe finger constructions and fittings are possible. The invention being thus disclosed, further variations will occur to those skilled in the art, and such variations are within the spirit of the invention, as defined by the following claims.

What is claimed is:

1. A temperature sensing probe comprising
   (a) a handle having a longitudinal axis, a first end and a second end, said second end including circuit forming means for interconnection with a temperature sensing element,
   (b) a probe finger structure extending from said second end, said finger structure including
      (i) a first portion extending along the longitudinal axis from the second end of the handle and constituting a narrow base portion of said finger structure,
      (ii) a second portion extending from the base portion and constituting an L-shaped intermediate portion of said finger structure,
      (iii) a third portion, having a first end connected with said second portion and oriented transverse to said first portion, said third portion having a second end constituting a tip of said finger structure,
   (c) a temperature sensing element, and
   (d) electrically conductive means extending within said first, second and third portions between said temperature sensing element and said circuit forming means,
   said temperature sensing element being mounted at said tip of said third portion and said tip having a cross-sectional dimension of under approximately one millimeter, said third portion being formed of a thermally insulative material and tapering progressively narrower from said first end to said tip, whereby when said tip is inserted in and surrounded by tissue to effect a temperature measurement the temperature sensing element is effectively supported in thermal isolation from overlying tissue.

2. A probe according to claim 1, further comprising means mounted in said handle for processing a signal from said temperature sensing element to develop a temperature indication indicative of the temperature of said element.

3. A probe according to claim 2, further comprising temperature display means, mounted in said handle for displaying the temperature sensed by the sensing element.

4. A probe according to claim 3, wherein the third portion includes markings for indicating depth of penetration.

5. A probe according to claim 4, further comprising twist-lockable coupling means for electrically and mechanically coupling the probe finger structure to the handle by a twist-lock motion thereof.

6. A probe according to claim 3, further comprising twist-lockable coupling means for electrically and mechanically coupling the probe finger structure to the handle by a twist-lock motion thereof.

7. A probe according to claim 3, wherein the temperature sensing element is a thermistor.

8. A probe according to claim 3, wherein the thermally insulative material has a thermal conductivity of less than approximately $10^{-2}$ watt/cm. °C.

9. A probe according to claim 1, wherein the temperature sensing element is a thermistor.

10. A probe according to claim 1, wherein the thermally insulative material has a thermal conductivity of less than approximately $10^{-2}$ watt/cm. °C.

* * * * *